United States Patent [19]

Cornu et al.

[11] Patent Number: 4,569,933
[45] Date of Patent: Feb. 11, 1986

[54] ANTIHYPERTENSIVE SUBSTITUTED DERIVATIVES OF 2,5-DIAMINO 1,4-DIAZOLE

[76] Inventors: Pierre-Jean Cornu, 100, Avenue Kleber, F-75116, Paris; Claude Perrin, 5, rue de l-Avenir, F-91400, Orsay; Bernard Dumaitre, 24, rue Chemin Vert., F-93000, Bobigny; Gilles Streichenberger, 30, boulevard du Chateau, F-92200, Neuilly sur Seine, all of France

[21] Appl. No.: 599,784

[22] Filed: Apr. 13, 1984

[51] Int. Cl.$^4$ .................. A61K 31/535; C07D 401/12
[52] U.S. Cl. ..................... 514/237; 514/252; 514/314; 514/318; 514/319; 514/321; 514/323; 514/324; 514/326; 544/98; 544/405; 546/168; 546/176; 546/193; 546/197; 546/201; 546/202; 546/205; 546/209; 546/210
[58] Field of Search ............... 546/197, 193, 205, 168, 546/176, 202, 209, 210, 201; 544/405, 98; 514/252, 237, 314, 318, 321, 324, 319, 323, 326

[56] References Cited

U.S. PATENT DOCUMENTS

| | | | |
|---|---|---|---|
| 3,238,215 | 3/1966 | Zenitz | 546/201 |
| 3,966,748 | 6/1976 | Hofmann et al. | 546/209 |
| 4,140,781 | 2/1979 | Huebner | 546/197 |
| 4,426,387 | 1/1984 | Archibald et al. | 546/197 X |

FOREIGN PATENT DOCUMENTS

| | | | |
|---|---|---|---|
| 7787M | 3/1970 | France | 546/201 |
| 2105223 | 4/1972 | France | 546/224 |
| 2183683 | 12/1973 | France | 546/199 |
| 2213059 | 8/1974 | France | 546/199 |

*Primary Examiner*—Richard A. Schwartz
*Attorney, Agent, or Firm*—Omri M. Behr

[57] ABSTRACT

This invention relates to new chemical compounds which are derivatives of 2,5-diaminodiazoles.

It relates more particularly to new 2-amino 5-(aralkylamino piperidino alkyl) diazoles.

These compounds and the acid addition salts thereof have interesting therapeutical properties, particularly anti-hypertensive properties which make them useful as active ingredient of pharmaceutical compositions.

10 Claims, No Drawings

ANTIHYPERTENSIVE SUBSTITUTED DERIVATIVES OF 2,5-DIAMINO 1,4-DIAZOLE

PRIOR ART

The prior art may be illustrated by the following references:
French Medicine Patent 7787M
U.S. Pat. No. 3,238,215 (5 B. L. Zenitz)
French Patent Application No. 2,213,059 (to Janssen)
French Patent Application No. 2,183,683 (to Sumitomo)
U.S. Pat. No. 3,966,748 (Corris Mabelle et al)
French Patent Application No. 2,105,223 (to John Wyeth)
U.S. Pat. No. 4,140,781 (C. F. Heubner)

SUMMARY OF THE INVENTION

This invention relates to novel derivatives of 2,5-diamino 1,4-diazole earing substituents on the amino group.

It specifically provides 2-amino5-(aralkyl piperidino alkyl amino)1,4-diazoles having the formula I.

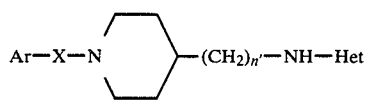

wherein Het is a heterocyclyl radical selected form the group consisting of
compounds having the formula A

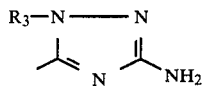

wherein R3 is hydrogen lower alkyl, aryl or aryllower alkyl and—compounds having the formula B

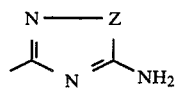

wherein Z is NH, NR3 or an oxygen.

This invention also relates to the acid addition salts of the said compounds.

The invention also discloses a process for producing the compounds of formula I.

The compounds of formula I are used in the form of pharmaceutical compositions intended for oral, parenteral or rectal routes of administration.

This invention relates to novel heterocyclic nitrogenous derivatives, the processes for their preparation and the pharmaceutical compositions containing them.

It has more particularly as an object novel derivatives of 2,5-diamino1,4-diazole, the amino groups of which may be substituted. Specifically this invention provides 2-amino5-[(aralkyl piperidino alkyl)amino]1,4-diazoles of the general formula I

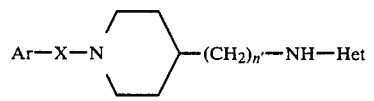

wherein Ar is an aryl or heteroaryl, mono or bicyclic radical.

X is an optionally-substituted alkylene chain selected from the group consisting of (CH2)n; CHOH—(CH2)n1; CO—(CH2)n1 and

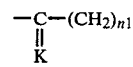

n is equal to 1, 2, 3 or 4
n1 is equal to 1, 2 or 3
n' is equal to 0, 1 or 2
K is a group

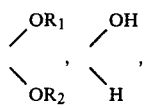

an alkylenedioxy chain, two hydrogens or the oxygen of a keto function.

Het is a radical selected from the group consisting of: the compounds having the formula A

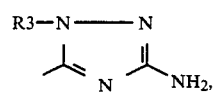

wherein R3 is hydrogen, a lower alkyl, an aryl lower alkyl radical and the compounds having the formula B

wherein Z is a radical —NH—, NR3 or an oxygen (wherein R3 is a lower alkyl, an aryl or an aryllower alkyl).

This invention also relates to the acid addition salts of the compounds of general formula I with a mineral or organic acid, preferably a therapeutically-compatible acid.

This invention also extends to the optical isomers of the compounds of general formula I. The molecule includes at least one asymmetric carbon and hence the dextro and laevo isomers may be resolved.

Moreover when Y is the chain—CHOH—(CH2)—n1 it gives rise to the formation of a novel center of asymmetry and it may be possible to isolate the resulting diastereo isomers which can be resolved into their optically active isomers.

Further when Ar is a partially saturated bicyclic radical, there is an extra asymmetric carbon atom giving rise to a supplemental possibility of resolution. The corresponding molecule may thus be written in the following manner:

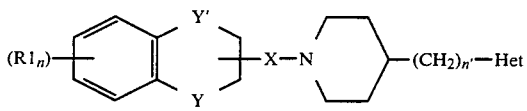

In this structure Y and Y' are the same or different and may be CH2— radical, or —O, S or NH.

When the substituent Z is oxygen the heterocyclic structure is that of a 2,5-diamino-3-oxa-1,4-diazole.

When the substituent Z is an imino group, the heterocyclic structure is that of a 2,5-diamino-1,3,4-triazole.

chain having 2, 3 or 4 carbon atoms, or a Ketalized oxo alkylene chain having 2, 3 or 4 carbon atoms.

The length and the nature of the alkylene chains as a function of the parameters, n, n1 and n' play an important role and determine the intensity or the duration of the pharmacological effects of the compounds of general formula I.

Among the compounds of general formula I the following subgroups may particularly cited as presently preferred (1) THE PHENYL ALKYL PIPERIDINE OF GENERAL FORMULA IA

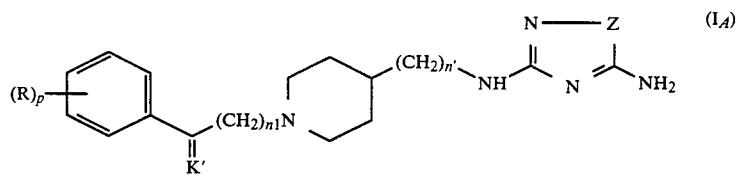

The latter may exist under one of the two tautomeric iminotriazole forms.

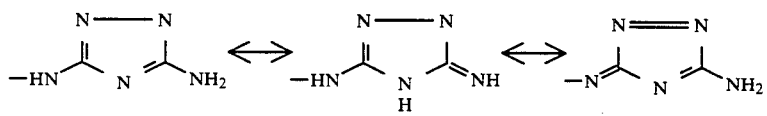

The several meanings of the Ar group include:
(a) the monocyclic aromatic radicals such as pyridine, oxazine, pyrazine and a phenyl radical of the general formula.

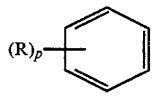

Wherein R is hydrogen, a lower alkyl radical, a lower alkoxy radical, a halogen, a trifluoromethyl, a sulphonamido radical, a trifluoromethoxy, a cyano radical, a carboxy radical, a carboxamido radical, a nitro group or an alkylene dioxy group and p is an integer of 1 to 3
(b) the saturated or partially saturated bicyclic aromatic radicals such as tetrahydronaphthyl, naphthyl-1 or -2, benzodioxanyl, benzodioxenyl, quinolinyl, triachromanyl or indolyl-2 or -3.

In a preferred manner the Ar-group is a substituted or unsubstituted phenyl, a pyridyl, a tetrahydronaphthyl or a benzodioxanyl radical.

The substituent X is a straight or branched chain having from 1 to 4 carbon atoms, a hydroxy alkylene wherein K' is two hydrogens, the group

(in which R1 and R2 are each a lower alkyl radical or together are an alkylene chain having from 2 to 4 carbon atoms) the group

or the oxygen of a Ketonic function.
n1 and n' have the previously-given meanings and Z is a group NH,
N—R3 or an oxygen (R3 is defined as previously), in the racemic or optically-active form.

(2) THE PHENYL ALKYL PIPERIDINES OF GENERAL FORMULA IB

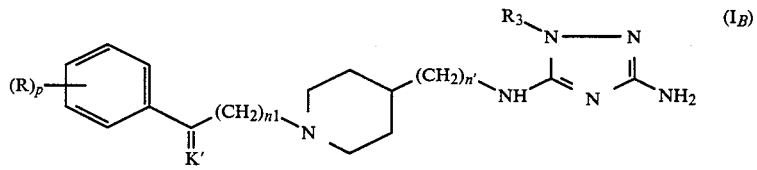

in which the substituents R, R3, K', p, n1 and n' are defined as previously.

(3) THE (BENZO 1,4-DIOXANYL)ALKYL PIPERIDINES OF GENERAL FORMULA IC

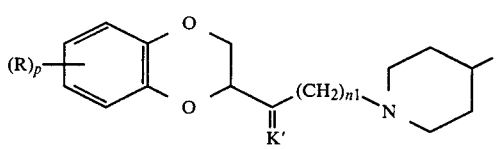 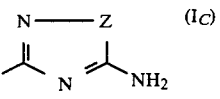

wherein R, K', Z, p, n' and n1 have the previous definitions. in the racemic or optically-active form.

(4) THE (BENZO 1,4-DIOXANYL)ALKYL PIPERIDINES OF GENERAL FORMULA ID

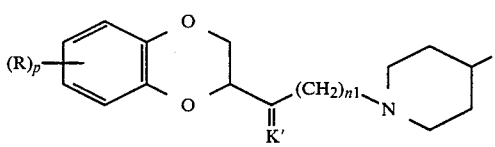 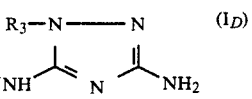

wherein the substituents R, K', R3, n1, n' and p have the previously-given definitions. in the racemic or optically-active form

(5) THE INDOLYL-(2 or 3)ALKYL PIPERIDINES OF GENERAL FORMULA IE

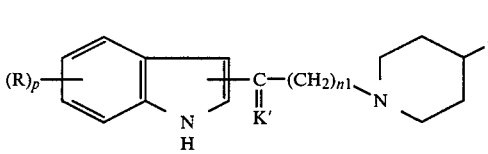 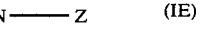

in which the substituents R, K', Z, p, n1 and n' are defined as previously given.

As far as the invention is concerned, a lower alkyl radical is a hydrocarbon radical having from 1 to 6 carbon atoms in a straight or branched chain, as for example methyl, ethyl, isopropyl, sec-butyl, tert-butyl, pentyl, neopentyl and n-hexyl.

A lower alkoxy radical has from 1 to 6 carbon atoms in the alkyl chain which may be straight or branched, such as a methoxy, ethoxy, isopropoxy, tert-butoxy, or a n-pentoxy.

The word halogen is intended to designate a chlorine, bromine, iodine, or fluorine atom. The preferred one is fluorine.

The word aryl is intended to designate an aromatic monocyclic, homo- or heterocyclic radical which may optionally be substituted by 1, 2 or 3 substituents selected from the group consisting of a lower alkyl, a halogen, a lower alkoxy, an alkylenedioxy and a trifluoromethyl.

The word aralkyl is intended to designate an aromatic radical defined as above, bearing a straight or branched alkyl chain having from 1 to 6 carbon atoms.

Among the acid addition salts of the compounds of general formula I, particularly preferred are the hydrochlorides, the hydrobromides, the sulphates, nitrates, phosphates, thiosulphates, formates, acetates, maleates, fumarates, benzoates, 2,6-dichlorobenzoate, nitrates, tartarates, methoxy salicylates, 3,4,5-trimethoxy benzoates, vanillinates, O-carbethoxy syringoates, naphtoates, benzene sulphonates, methane sulphonates, isothionates, nicotinates, isonicotinates, embonates and the glucose-phosphates.

As acid addition salts which may not be used for therapy, it may be cited the iodates, perchlorates, thiocyanates, ferrocyanides, oxalates, flavinates or Reineckates. They may be used as identification, purification or isolation reagents.

The compounds according to this invention are endowed with interesting pharmacological properties and particularly with anti-hypertensive properties correlated with a only slight depressive action on the CNS. Due to their high level of activity, the compounds of general formula I or their acid addition salts find therapeutic use as active ingredients of medicines intended to counteract or to reduce the effects of the hypertensive condition.

For these purposes they are utilized in the form of pharmaceutical compositions designed for parenteral, oral, rectal or sublingual ways of administration.

The pharmaceutical compositions include, as active ingredient at least one compound of general formula I or an acid addition salt thereof with a mineral or organic acid, in admixture or conjunction with an inert therapeutically-acceptable carrier or vehicle.

As preferred administration forms there may be mentioned coated or uncoated tablets, capsules, dragees, multicore tablets, drops, drinkable solution or suspensions; injectable solutions or suspensions packed in ampules, multidosage flasks or auto-injectible syringes; the suppositories and sublingual tablets.

The pharmaceutical compositions according to this invention, may further contain one or more active ingredients having a similar, complementary or synergistic action. In this respect there may be mentioned diuretic agents of the thiazidic type or of the triamino pteridine type; beta-blocking agents such as propranolol, pindolol or atenolol.

The daily dosage may range within broad limits as a function of the therapeutic use, the way of administration, the age of the patient and the duration of the hypertensive condition.

Usually in the adult, the dosage ranges from 1 mg and 50 mg per unit dosage and from 1 mg and 150 mg per day. In a preferred manner, the pharmaceutical compositions according to this invention contain from 1 to 25 mg per unit dosage of active ingredient in the form of the free base or of a salt thereof.

This invention further extends to a process for preparing the compounds of general formula I characterized in that a N-cyano isothio- or iso Urea of general formula II

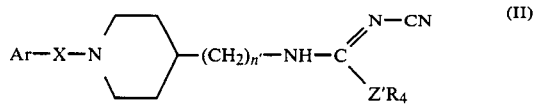

wherein Ar, X and n' have the previously given meanings.

Z' is oxygen or sulphur and R4 is a lower alkyl radical is reacted with an aminated derivative of the general formula III

HZ—NH2               (III)

wherein Z is defined as above —to produce—when Z is oxygen—a 2-amino-3-oxa 1,4-diazole of general formula I'

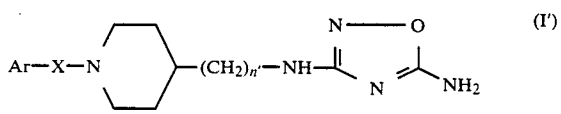

when Z is an imino NH radical, a 2-amino-1,3,4-triazole of formula I"

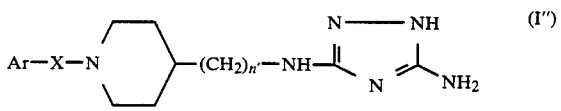

and when Z is a N—R3 radical—a mixture of 2-amino 1,3,4-triazole of formula

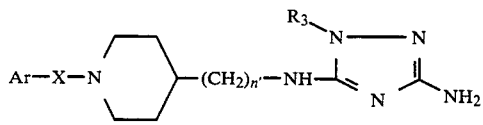

and

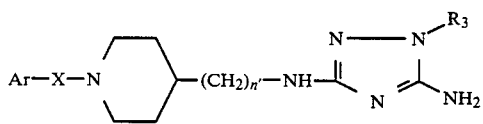

which are separated by physical means. When X is a

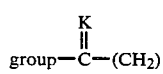

n1, wherein K is a group

(R1 and R2 are defined as previously) it is possible to hydrolyse the resulting Ketal with a mineral or organic acid or by exchange of functions with a carbonylated acid, to obtain a carbonyl derivative of general formula IV.

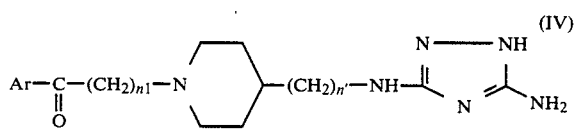

wherein Ar, n1, n' and Het are defined as previously
The carbonylated compounds of formula IV may be further reduced into an alkylated derivative using hydrazine in the conditions of the Wolff-Kishner's reaction or zinc and hydrochloric acid in the conditions of the Clemmensen reaction to produce an alkylated derivative.

The resolution of the compounds of formula I may be carried out by salification with an optically-active acid such as d-tartaric acid, dibenzoyl d-tartaric acid, diethyl d-tartramic acid, pimaric acid, abietic acid, d-camphosulphonic acid, optically—active naphthalene dioxyphosphonic acid or glucose-6 (or 1) phosphoric acid.

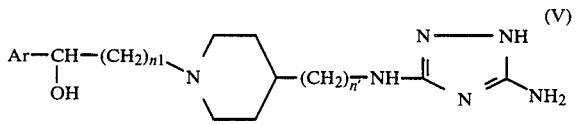

The carbonyl derivative may also be reduced to an alkyl derivative by hydrazine in the conditions of the Wolff-Kisher's Reaction or by Zinc in Chlorhydric medium in the conditions of the Clemmensen's Reaction to produce an alkylated derivative.

The resolution of the compounds of general formula I may be carried out by salifying them by means of an optically-active acid such as d-tartaric acid, d-dibenzoyl tartaric acid, d-diethyl tartramic acid, pimaric acid, abietic acid, d-camphosulphonic acid, optically-active naphthalenedioxyphosphonic acid or glucose 6 (or 1) phosphoric acid.

The cyano isoureas or isothioureas used as starting material having the general formula II are prepared according to a process which consists in that a 4-aminopiperidine of general formula VI

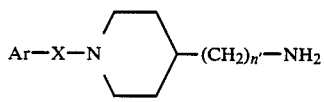

wherein the substituents Ar, X, and n' are defined as previously is reacted with a cyano iminating agent selected from the group consisting of
    the alkyl cyanoimino isothiocarbonate of general formula VII

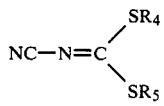

wherein R4 and R5 are lower alkyl radicals and the alkyl mixed cyanoiminoisothiocarbonate of the general formula VIII

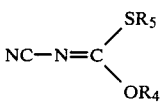

wherein R4 and R5 are defined as previously.

to produce the isothiourea or the isourea of the general formula II

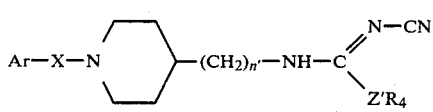

wherein the substituents Ar, R4 and n' are defined as previously and Z is oxygen or sulphur.

The following examples are intended to illustrate the invention without limiting in any manner

EXAMPLE I

1-[(1,4-benzodioxan-2-yl)-methyl]-4-[(2-amino-S-triazol-5-yl)-aminomethyl]-piperidine A mixture of 7.2 g of 1-[(1,4-benzodioxan-2yl)-methyl]-4-(N-cyano-S-methylisothioureidomethyl)-piperidine, 4.5 ml hydrazine hydrate and 100 ml ethanol are heated to reflux for 4 hours. This solution is then concentrated to dryness to give a pasty product which after treatment with acetonitrile provides colourless crystals. These are separated by filtration, washed and dried.

5 g of the desired compound are thus obtained and recrystallized from ethyl acetate. Its melting point is 157°–158°.

EXAMPLE II

1-[(1,4-benzodioxan2-yl)-methyl]-4-[2-amino-s-triazolyl-5-yl)-amino]-piperidine

A mixture of 4 g 1-(1,4-benzodioxan-2yl)methyl-4-(N-cyano-S-methyl isothioureido)-piperidine and 4 ml hydrazine hydrate in 100 ml ethanol are heated to reflux for 4 hours. It is concentrated to dryness and the resulting paste is taken up in acetonitrile giving rise to the recovery of 3.2 g of white crystals.

These are purified by recrystallization from isopropanol. The desired 1-(1,4-benzodioxan2-yl)-methyl)-4-(2-amino-S-triazol5-yl)-aminopiperidine is thus obtained, melting at 215°–216°.

EXAMPLE III 1-(1,4-benzodioxan2-yl)-methyl-4-[(2-amino 1,3,4 oxadiazol-5-yl)-amino]-piperidine A mixture of 7 g 1-[(1,4-benzodioxan-2-yl)-methyl]-4-(N-cyano-S-methyl isothioureido)piperidine, 4.2 g hydroxylamine hydrochloride 5,2 g sodium bicarbonate and 20 ml ethanol is heated to reflux for 4 hours. The solution is then concentrated to dryness which allows the recovery of a vitreous solid. The latter is taken up in acetonitrile. It dissolves first then it crystallizes. The crystals are filtered, washed with acetonitrile and dried.

2,9 g of the sought compound is obtained.

It shows a double melting point: first melting at 141°–142° then solidification and melting at 167°–168°.

EXAMPLE IV

1-[(1,4-benzodioxan-2yl)-methyl]-4-[(2-amino-S-triazol-5-yl)amino methyl]-piperidine A mixture of 5.5 g of 1-(1,4benzodioxan-2-yl)-methyl-4-(N-cyano-S-methyl isothioureido methyl)-piperidine, 4.5 ml hydrazine hydrate and 100 ml ethanol are heated to reflux for 4 hours.

After concentration to dryness, a paste is recovered which crystallizes after grinding with acetonitrile. The crystals are filtered, washed with acetonitrile and dried. They are purified by recrystallization from isopropanol giving rise to the recovery of 5 g of the desired product which melts at 148°.

EXAMPLE V

1-[(1,4-benzodiozan-2-yl)ethyl]-4-[(2-amino1,3,4-oxadiazol-5-yl)aminomethyl]-piperidine A mixture of 7.5 g 1[(1,4-benzodioxan-2-yl)-ethyl]-4-(N-cyano-5-methyl isothioureido methyl)piperidine, 2.1 g hydroxylamine hydrochloride, 5.1 g sodium bicarbonate in 100 ml is heated to reflux for 20 hours.

After filtration, the mixture is concentrated to dryness to give a semi-solid oil which is redissolved in 50 ml hot isopropanol. on cooling, the solution crystallizes soon and the crystals are filtered and dried.

After purification and recrystallization from ethanol, 2.6 g of the desired product are recovered which crystallizes with 0.5 mol water. It shows a double melting point: melting first at 75° then solidification and remelting at 128°.

The starting material 1-[(1,4-benzodioxan-2-yl)-ethyl]-4-(N-cyano-S-methyl isothioureido methyl)-piperidine is prepared as follows: A mixture of 73 g 1-[(1,4-benzodioxan-2-yl)-ethyl]-4-aminomethyl piperidine and 38.6 g methyl N-cyano imino dithiocarbonate in 500 ml ethanol is heated for 4 hours to the reflux. The compound which crystallizes by reversion to room temperature is filtered, washed with ethanol and dried.

85 g of the desired product are thus obtained as white crystals showing a double melting point (melting at 145° then solidification and remelting at 155°).

EXAMPLE VI

1-[(6-methyl-1,4-benzodioxan-2-yl)-methyl]-4-[(2-amino-S-triazol-5-yl)aminomethyl]-piperidine

STEP A

1-[(6-methyl-1,4-benzodioxan-2yl)-methyl]-4-N-cyano-S-methyl isothioureidomethyl)-piperidine A mixture of 58.4 g 1-[(6-methyl1,4-benzodioxan-2yl)methyl]4-aminomethyl piperidine and 31 g of dimethyl N-cyano imino isodithiocarbonate in 400 ml ethanol is heated to reflux for 4 hours. The compound which crystallizes after cooling is filtered, washed with ethanol and dried. It appears as white crystals melting at 145°.

STEP B 7.5 g 1-[(6-methyl1,4-benzodioxan-2-yl)-methyl]-4-(N-cyano-S-methylisothioureido)-piperidine are heated at reflux for 4 hours with 4.5 ml hydrazine hydrate in 100 ml ethanol after concentration to dryness, a paste is obtained which, after being taken up in acetonitrile, crystallizes. 6.5 g of white crystals are thus obtained which are purified by recrystallization from isopropanol. 1-[(6-methyl-1,4-benzodioxan-2yl)methyl]-4-[(2-amino-S-triazol-5-yl)aminomethyl]-piperidine appears as about colourless crystals which melts at 138°.

EXAMPLE VII

1-[(6-methyl-1,4-benzodioxan-2yl)methyl]-4-[(2-amino 1,3,4-oxadiazol-5-yl)aminomethyl]-piperidine A mixture of 7.5 g of 1-[(6-methyl-1,4-benzodioxan-2-yl)-methyl]-4-(N-cyano S-methylisothioureidomethyl)-piperidine, 4.2 g hydroxylamine hydrochloride and 10.2 g sodium bicarbonate in 100 ml ethanol is heated at the reflux for 20 hours.

After filtration the ethanolic solution is concentrated to dryness and the dry residue is taken up with water then extracted with chloroform. The organic phase is separated, dried and concentrated to dryness. 5.7 g of the compound are obtained. The latter is recrystallized from isopropanol. It melts at 146°.

EXAMPLE VIII 1-(1,4-benzodioxan-2-yl)-methyl-4-[(2-amino-1,3,4-oxadiazol-5-yl)-aminomethyl]-piperidine A mixture of 7.2 g 1-[(1,4-benzodioxan-2-yl)-methyl]-4-(N-cyano-S-methyl isothioureido methyl)piperidine, 2.1 g hydroxylamine hydrochloride and 5.1 g sodium bicarbonate in 100 ml ethanol is heated to reflux for 4 hours.

After filtration, the filtrate is concentrated to dryness giving rise to the production of semi solid uncrystallisable amorphous compound.

The compound is purified by chromatography through a column filled with silicaH-(Merck) and elution with a mixture of chloroform-isopropylamine (9,1)

The compound obtained after elution and evaporation of the solvent then crystallizes after being taken up in a minimum amount of acetonitrile. 3.8 g of the desired product are thus recovered as white crystals melting at 130°-131°.

EXAMPLE IX

1-[(1,4-benzodioxan-2-yl)-2-hydroxyethyl]-4-[(2-amino-1,3,4-oxadiazol-5-yl)-aminomethyl]-piperidine

STEP A

1-[(1,4-benzodioxan-2-yl)-2-hydroxyethyl)]-4-(N-cyano-S-methylisothioureidomethyl)-piperidine A mixture of 58 g 1-[(1,4-benzodioxan-2-yl)-2-hydroxyethyl]-4-aminomethyl piperidine and 29 g dimethyl N-cyano imino dithiocarbonate in 400 ml ethanol is heated to the reflux for 4 hours. The resulting solution is then concentrated to dryness and taken up in isopropyl ether giving rise to the recovery of crystals which are separated by filtration, washed with isopropyl ether and dried.

By recrystallization from isopropanol, 58 g of the desired product are obtained which melts at 128°.

STEP B 7.8 g of 1-[(1,4-benzodioxan-2-yl)-2-hydroxyethyl]-4-(N-cyano S-methyl isothioureido methyl)piperidine 2,1 g hydroxylamine hydrochloride and 5.1 g sodium bicarbonate in 100 ml ethanol are mixed together and heated at reflux for 20 hours. After filtration, the reaction mixture is concentrated to dryness and a pasty solid is recovered which is taken up in hot isopropanol. After 24 hours standing, a solid has precipitated which is separated by filtration, washed with isopropyl ether and recrystallized in the minimal amount of ethanol.

1.7 g of the desired product are thus obtained as crystals retaining 0.5 mol water of crystallization. The compound melts at 148°-150°.

EXAMPLE X

1-[(1,4-benzodioxan-2-yl)-2-hydroxyethyl]-4-(2-amino-S-triazol-5-yl)-aminomethyl]-piperidine A mixture of 7.8 g of 1-[(1,4-benzodioxan-2-yl)-2-hydroxyethyl]-4-(N-cyano-S-methylisothioureidomethyl)-piperidine obtained according to the procedure of example 8 step A and 5 ml hydrazine hydrate in 100 ml ethanol is heated to reflux for 4 hours. After concentration to dryness, a paste is obtained which becomes solid after treatment with acetonitrile. The product is filtered, washed with isopropyl ether, dried then recrystallized from isopropanol.

2 g of the desired product are thus obtained as crystals melting at 164°.

EXAMPLE XI

1-[(1,4-benzodioxan-2-yl)-methyl]-4-[(2-amino-3-methyl-S-triazol-5-yl)-aminoethyl]-piperidine and
1-[(1,4-benzodioxan-2-yl)-methyl]-4-[(2-amino-4-methyl-S-triazol-5-yl)-methyl]-piperidine 3.6 g of 1-[(1,4-benzodioxan-2-yl)-methyl]-4-(N-cyano-S-methylisothioureidomethyl)-piperidine, 8 ml methyl hydrazine, and 50 ml ethanol are heated at reflux for 18 hrs. After concentration to dryness, an oily residue is recovered which shows, by TLC, two different spots using as eluting solvent the mixture chloroform—isopropylamine 9:1—The two compounds are eluted on a column filled with silicaH (Merck) with the mixture chloroform—isopropylamine 9:1. There is thus obtained 1.4 g of a first compound eluted at first as an oily product which crystallizes when treated with isopropyl ether.

This compound corresponds to the 3-methyl derivative. It melts at 129°-130°.

Continuing the elution, 0.7 g of an oily product is separated, which crystallizes by treatment with isopropyl ether. It corresponds to the 4-methyl derivative. This compound melts at 139°-140°.

When using instead of methylhydrazine, phenylhydrazine in a similar fashion a mixture of 3-phenyl and 4-phenyl derivatives is obtained which is separated through chromatography on silica.

When using in the same manner p-methoxy phenyl hydrazine, a mixture of 3-(4-methoxyphenyl) and 4-(4-methoxyphenyl) derivatives are obtained which may be separated through chromatography on a column of silica.

When using isopropylhydrazine, a mixture of 3-isopropyl and 4-isopropyl derivatives is obtained in a similar fashion which may be separated through chromatography on a column of silica.

EXAMPLE XII 1-(4-phenyl-4-oxobutyl-1)-4-(2-amino-S-triazol-5-yl-aminomethyl)-piperidine

STEP A 1-(4-phenyl-4,4-ethylenedioxybutyl-1)-4-(N-cyano-S-methylisothioureidomethyl)-piperidine A solution of 82.3 g of 1-(4-phenyl-4,4-ethylenedioxybutyl-1)-4-aminomethyl piperidine and 39.5 g dimethyl N-cyano imino dithiocarbonate in 400 ml ethanol is heated at reflux for 4 hours. The whole mixture is then concentrated to dryness and the resulting oily residue is taken up in isopropyl ether.

105 g of the desired product are obtained as white crystals melting at 136°.

STEP B 8 g 1-(4-phenyl-4,4-ethylenedioxybutyl-1)-4-(N-cyano-S-methylisothioureidomethyl)-piperidine are heated at reflux for 4.5 ml hydrazine hydrate in 100 ml ethanol.

The mixture is concentrated to dryness and the vitreous oily residue thus obtained is let crystallize by solution in ethyl acetate then cooling. 6.3 g of a compound melting at 134° is thus obtained.

This Ketal is hydrolysed by dissolving it in 150 ml N solution of hydrochloric acid and let stand for 18 hours at room temperature.

The solution is adjusted to a pH value of 10 with a solution of sodium hydroxyde giving rise to a crystallization. After filtration, washing of the precipitate with water and drying, 5,2 g of the product are obtained which is further recrystallized from isopropylalcohol. The pure compound melts at 154°.

EXAMPLE XIII 1-(4-phenyl-4-oxobutyl-1)-4-[(2-amino-1,3,4-oxadiazol-5-yl)-aminomethyl]-piperidine A mixture of 16.1 g 1-(4-phenyl-4,4-ethylenedioxybutyl-1)-4-(N-cyano S-methyl-isothioureidomethyl)-piperidine, 7.2 g hydroxylamine hydrochloride and 8.4 g sodium bicarbonate in 200 ml ethanol are heated at reflux for 18 hours. After filtration, the filtrate is concentrated ting vitrebus semi-solid residue is let crystallized by taking up in hot ethyl acetate. The crystals are filtered, washed and dried. 6.1 g of a colourless product is obtained which melts at 126°.

The thus produced Ketal is hydrolysed by dissolving it in 150 ml of hydrochloric acid. The solution is kept for 18 hours at room temperature. The medium is made basic by adding a solution of sodium hydroxide giving rise to the separation of an oily product which crystallizes by scratching. After filtration, washing with water and drying, 5 g of the desired Ketonic derivative are obtained. It is recrystallized from isopropanol—It melts at 80°-82°.

EXAMPLE XIV 1-(4-p-fluorophenyl)-4-oxobutyl-1)-4-[(2-amino-S-triazol-5-yl)-aminomethyl]-piperidine 33.6 g of 1-(4-p-fluorophenyl-4,4-ethylenedioxybutyl-1)-4-(N-cyano-S-methylisothioureido methyl)piperidine, 15 ml hydrazine hydrate and 400 ml ethanol are mixed together then heated at reflux for 16 hours. After concentration to dryness, a strongly viscous oil is recovered which cristallized when taken up in ethyl acetate.

27.5 g of the crystallized product are recovered which melts at 145°. The Ketal is then hydrolysed by dissolving it in 600 ml of N-hydrochloric acid and keeping it for 18 hours at room temperature.

The medium is thereafter made basic by adding to it sodium hydroxide to a pH value of 10, the precipitate is filtered and washed with water and dried.

25 g of colourless crystals are thus recovered. They are recrystallized from acetonitrile. Melting point 165° then solidifcation and remelting at 185° (double melting point).

EXAMPLE XV 1-(4-p-fluorophenyl 4-hydroxybutyl-1)-4-[(2-amino-S-triazol-5-yl)amino methyl]-piperidine To a solution of 3.9 g of 1-(4-p-fluorophenyl-4-oxobutyl-1)-4-[(2-amino-S-triazol-5-yl)-aminomethyl]-piperidine in 100 ml methanol chilled to 10°, 1 g sodium borohydride is added portionwise while stirring.

After one and half hour stirring at room temperature, some crystals appear. These are filtered, washed with water and with ethanol, and thereafter recrystallized from ethanol. 2.1 g of the desired product are recovered as colourless crystals melting at 210°.

EXAMPLE XVI 1-(4-p-fluorophenyl-4-oxobutyl-1)-4-[(2-amino-1,3,4-oxadiazol-5-yl)-aminomethyl]-piperidine 3.6 g hydroxylamine hydrochloride and 4.2 g sodium bicarbonate are suspended in 100 ml ethanol. To this 1-(4-p-fluorophenyl 4,4-ethylenedioxybutyl-1)-4-(N-cyano-S-methylisothioureidomethyl)piperidine is added and the whole mixture is heated at reflux for 17 hours; After filtration the solution is concentrated to dryness. The thus formed Ketal appears as a vitreous oily residue which is dissolved in 200 ml N-solution of hydrochloric acid to hydrolyse the Ketal function.

20 hours later at room temperature this solution is made basic with sodium hydroxide and extracted with chloroform. The organic phases are evaporated and the resulting oil is purified by chromatography through a column filled with silica H (Merck) using the mixture chloroform: 9—Isopropylamine: 1 as the eluting solvent. 2.9 g of an oily residue are thus obtained. When taken up in acetonitrile it crystallizes. The desired product is recovered as colourless crystals melting at 134°.

EXAMPLE XVII 1-(4-p-fluorophenyl-4,4-ethylenedioxy-butyl-1)-4-[(2-amino 3-methyl-S-triazol-5-yl)-aminomethyl]-piperidine and 1-(4-p-fluorophenyl-4,4-ethylenedioxybutyl-1)-4-[(2-amino 4-methyl-S-triazol-5-yl)-aminomethyl]-piperidine.

A mixture of 40 g 1-[4-p-fluorophenyl-4,4-ethylenedioxybutyl-1)-4-(N-cyano-S-methyl-isothioureidomethyl)-piperidine and 100 ml methylhydrazine in 300 ml ethanol is heated at reflux for 18 hours. After evaporation to dryness, 47 g of an oily residue are obtained which is redissolved in the hot in 250 ml acetonitrile. The solution crystallizes after a night standing. The crystalls are separated, filtered, washed with acetonitrile and dried.

14 g of a colourless compound are thus obtained, melting at 100° and homogenous by TLC (Rf=0.25)—The mother liquors are concentrated to dryness. The oily dry residue show by TLC two spots (one of Rf=0.25 and the other of Rf=0.1).

The two compounds are separated by chromatography on a column filled and 1.6 kg silica H (Merck) and eluting with the mixture Chloroform—isopropylamine.

EXAMPLE XVIII 1-(4-p-fluorophenyl-4-oxobutyl-1)-4-[(2-amino-4-methyl-S-triazol-5-yl)aminomethyl]-piperidine 12.5 g 1-(4-p-fluorophenyl-4,4-ethylenedioxybutyl-1)-4-[(2-amino-4-methyl-S-triazol-5-yl)-aminomethyl]-piperidine are dissolved in 500 ml of N hydrochloric acid and kept for 17 hours at room temperature. The medium is then made basic by adding sodium hydroxyde and extracted with ethyl acetate. The organic phase is washed with water, dried and concentrated. An oily residue is thus obtained which, taken up with acetonitrile, gives rise to the recovery of 3.9 g colourless crystals. 1-(4-p-fluorophenyl-4-oxobutyl-)-4-[(2-amino-4-methyl-S-triazol-5-yl)-aminomethyl]-piperidine melts at 114°–115°.

EXAMPLE XIX 1-(4-p-fluorophenyl-4-oxo-butyl-1)-4-[(2-amino-3-methyl-S-triazol-5-yl)-aminomethyl]-piperidine A solution of 3.5 g 1-(4-p-fluorophenyl-4,4-ethylenedioxybutyl-1)-4-[(2-amino-3-methyl-S-triazol-5-yl)aminomethyl]-piperidine is made in 100 ml N-hydrochloric acid and let stand for 18 hours at room temperature. The aqueous solution is then made basic by adding sodium hydroxyde and extracted with ethyl acetate. After concentration of the organic solution, a solid residue is recovered which is recrystallized from acetonitrile.

1.3 g of the desired compound are obtained as crystals melting at 162°.

EXAMPLE XX 1-(4-p-fluorophenyl-4-oxobutyl-1)-4-[(2-amino-4-methyl-1,3,4-triazol-5-yl)-aminomethyl]-piperidine

STEP A

A mixture of 10.65 g benzaldehyde and 4.6 g methylhydrazine in ethanol is heated to reflux for 30 mn. It is thereafter concentrated to dryness and benzaldehyde N-methyldrazone is recovered as a light oil. It is taken up in 100 ml ethanol and to this 14,6 g dimethyl N-(cyano-imino) dithio carbonate are added. The whole mixture is heated to reflux for 2 hours then the solvent is distilled off. The oily residue is recovered and crystallizes by scratching with isopropyl ether.

The crystals are filtered, washed and dried to yield N-(cyanoimino) (methylthiomethyl)-N-methyl-N'-benzylidenyl hydrazine as colourless crystals melting at 114°.

STEP B

A mixture of 3.25 g of the hydrazine of step A, 4.5 g of 1-[(4-p-fluorophenyl-4,4-ethylenedioxy)butyl-1]-4-aminomethyl-piperidine in 50 ml ethanol is heated to reflux for 2 hours. The solvent is then distilled off. The resulting orange oily residue is redissolved in 100 ml 2N hydrochloric acid.

The acidic solution is heated to reflux for 15 mn, then kept acid for 18 hours at room temperature. The aqueous solution is extracted with ether to eliminate benzaldehyde then made basic by adding sodium hydroxide. It is then extracted with ethyl acetate. The organic phases are separated, washed with water, dried and distilled off. The oily residue weighing 4.75 g is taken up with some ether from which it crystallizes. The triazolic derivative is thereafter recrystallized from the minimal amount of acetonitrile. The pure compound weighing 1.4 g is obtained as crystals melting at 96°.

This compound has the same IR spectrum than the isomer melting at 114°–115° obtained from the mixture produced with methylhydrazine. Similarly by TLC the Rf in the mixture chloroform-isopropylamine (9:1) are identical.

The difference between the two melting points may be explained by the fact that the compound melting at 96° retains a mole of water of crystallization as evidenced by micro analysis.

The other isomer obtained from the mixture and melting at 162° is undoubtedly the (2-amino-3-methyl-S-triazol-5-yl)aminomethyl derivative.

EXAMPLE XXI

1-[(Indol-3-yl)-ethyl]-4-[(2-amino-S-triazol-5-yl)-amino]-piperidine

STEP A

1-[(indol-3-yl)-ethyl)]-4-acetylamino-piperidine

A mixture of 18.7 g of 4-acetylamino-piperidine, 29.5 g of 3(2-bromoethyl) indole and 13.3 g triethyl amine previously dissolved in 70 ml dimethyl formamide is stirred for 20 hours at room temperature. After concentration to dryness the residue is taken up in the minimal amount of water containing few ml of ammonia.

The aqueous phase is then extracted with chloroform. The chloroformic solution is washed with water, dried and distilled off. 30 g of the desired product are thus obtained as colourless crystals melting at 160°.

After purification by recrystallization from acetonitrile, the pure compound is recovered which melts at 165°.

STEP B

1-[(Indol-3-yl)-ethyl]-4-amino-piperidine 26 g 1-(indol-3-yl)ethyl-4-acetylamino piperidine obtained at step A are dissolved in 260 ml 2N hydrochloric acid then the soluition is progressively heated to reflux and held for 2 and half hours. After cooling the reaction medium is filtered and the filtrate is made basic by adding concentrated aqueous sodium hydroxyde. An oily precipitate appears which quickly becames solid and crystalline.

The crystals are separated, dried, rinsed with water and dried. 23 g of the aminopiperidine are thus obtained as cream-coloured crystals melting at 105°–110°.

By TLC the compound is homogenous (only one spot at Rf=0.45) using the mixture-methanol-isopropylamine (9:1) as the eluting solvent. The compound is pure enough to be used as such for the next step of the synthesis.

STEP C

1-[(Indol-3-yl)-ethyl)-4-(N-cyano-S-methyl-isothioureido)-piperidine

To a mixture of 13.25 g dimethyl N-cyano imino isothiocarbonate and 300 ml ethanol 24 g 1-[Indol-3-yl)-ethyl]-4-amino-piperidine are added and heated to reflux for 4 hours. The insoluble matters are separated and ground with ether. The resulting crystals are filtered, then washed and dried. 27 g of the isothiourea are thus recovered (MP=44°)

STEP D

1-[(Indol-3-yl)-ethyl]-4-[2-amino-S-triazol-5-yl)]-aminopiperidine 6.8 g of 1-[(Indol-3-yl)-ethyl]-4-(N-cyano-S-methyl isothioureido)piperidine and 4 ml 5 hydrazine hydrate are dissolved in 100 ml ethanol.

The whole mixture is heated to reflux for 20 hours then the solvent is distilled off. An orange oil is recovered which, after having been taken up in acetonitrile, crystallizes after few hours. The crystals are separated, rinsed, washed with ether and dried. 5.6 g of the desired triazole are thus obtained. The latter is purified by recrystallizing it from ethanol. It melts at 200°. The pure compound retains ½ mol of water of crystallization.

EXAMPLE XXII 1-(Indol-3-yl ethyl)-4-[(2-amino-S-triazol 5-ylamino)methyl]-piperidine

STEP A

1-[(Indol-3-yl)-ethyl]-4-piperidino carboxamide 22.4 g 3(2-bromo ethyl) Indole, 12,8 g piperidino-4 carboxamide and 10.1 g triethylamine are suspended in 200 ml dimethylformamide. After 18 hours stirring, the mixture is concentrated to dryness and the oily residue is ground, with ammonia water until the crystallization initiates. After one night standing in a cool place, the crystals are separated by filtration, washed with water then with hexane and dried. The crystals are recrystallized from ethanol and finally 19 g 1-[(Indol-3-yl)-ethyl]-piperidino 4-carboxamide are recovered as colourless crystals melting at 184°.

By TLC the compound is homogeneous (a spot of Rf 0.70 with the eluting system methanol:isopropylamine 9:1)

STEP B

1-[(Indol-3-yl)-ethyl]-4-aminomethyl-piperidine

A suspension of 10 g lithium aluminohydride in 150 ml tetrahydrofuran is prepared and to this, while stirring and avoiding any increase of temperature, 20 g 1-[(Indol-3-yl)-ethyl]-piperidino 4-carboxamide are added—Once the addition achieved, the mixture is heated for 4 hours at the reflux of the solvent. The excess of reagent is destroyed by cautious addition of water while maintaining strong cooling to avoid a temperature increase above 0°. The mixture is filtered on a special clay sold under the trade name CELITE. The filtrate is evaporated off. An oily residue is recovered and the latter is taken up in the minimal amount of ethanol. The ethanolic solution is filtered then evaporated to dryness anew.

19 g of the desired amino methyl piperidine are thus produced as a liquid compound which progressively crystallizes.

The compound has a double melting point: 80° then after solidification 130°–132°.

STEP C

1-[(indol-3-yl)-ethyl]-4-(N-cyano-S-methyl isothioureido methyl)-piperidine

A mixture of 18.8 g 1-(indol-3-yl-ethyl)-4-amino methyl-piperidine and 10.7 g methyl N-cyanoimino dithio carbonate in 300 ml ethanol is heated for 4 hours at the reflux. The mixture is let to chill then concentrated to dryness. The recovered oily product is taken up in ether until initiation of the crystallization. The crystalline suspension is kept aside then filtered. The crystals are dried, rinsed with ether, and dried. 18 g of 1-[(Indol-3-yl)-ethyl]-4-(N-cyano-S-methyl isothioureido methyl)-piperidine are thus obtained as colourless crystals melting at 150°.

STEP D

1-[(Indol-3-yl)-ethyl]-4-[(2-amino-S-triazol-5-yl)-aminomethyl]-piperidine

A solution of 7.1 g 1-[(Indol-3-yl)-ethyl])-4-(N-cyano-S-methyl)-piperidine and 4 ml hydrazine hydrate in 100 ml ethanol is heated to reflux for 18 hours.

After concentration to dryness, the residue is taken up in acetonitrile from which the compound crystallizes. The suspension is kept aside for some hours then filtered. The crystals are washed with acetonitrile then dried under vacuum. 6.3 g of the desired triazole are then obtained. It appears as colourless crystals melting at 172°.

EXAMPLE XXIII

Using the same procedure than in example I or in example XIV the following compounds have been prepared:

1-(4-(p-fluorophenyl-4-oxobutyl-1)-4-(2-amino-1,3,4-triazolyl-5)aminopiperidine MP=216°

1-(4-(p-fluorophenyl-4-oxobutyl-1)-4-(2-amino-1,3,4-oxadiazolyl-5)aminopiperidine MP=186°

1-(4-(p-fluorophenyl-4-oxobutyl-1)-4-(2-amino-4-methyl-1,3,4-triazolyl-5)aminopiperidine MP=152°

1-(4-(p-fluorophenyl-4-oxobutyl-1)-4-(2-amino-3-methyl-1,3,4-triazolyl-5)-aminopiperidine MP=162°

1-[2-(indolyl-3-yl)ethyl]-4-[2-amino-1,3,4-oxadiazolyl-5)-aminomethyl]-piperidine.

EXAMPLE XXIV

Tablets containing 2.5 mg active ingredient

| | |
|---|---|
| 1-(4-p-fluorophenyl-4-oxobutyl-1)-4-[(2-amino-1,2,4-oxadiazol-5-yl)amino methyl]-piperidine | 25 g |
| wheat starch | 650 g |
| Lactose | 175 g |
| Microcrystalline cellulose | 45 g |
| Calcium phosphate | 900 g |
| Magnesium stearate | 25 g |
| Carboxymethyl starch | 17.5 g | for 10.000 tablets finished at an average weight of 0.185 g.

EXAMPLE XXV

Tablets containing 5 mg of active ingredient

| | |
|---|---|
| 1-[(benzodioxan-2-yl)-methyl]-4-[(2-amino-1,3,4-triazol-5-yl-methylamino]-piperidine | 50 g |
| Wheat starch | 400 g |
| Maize starch | 220 g |
| Microcrystalline cellulose | 375 g |
| Calcium sulphate | 510 g |
| Carboxymethyl cellulose | 20 g |
| Ethyl cellulose | 15 g | for 10.000 tablets finished at an average weight of 0.150 g.

EXAMPLE XXVI

Pharmacological study of the compounds according to this invention.

(a) Determination of the Acute Toxicity

An approximative average lethal dosage has been determined after administration by oral way of the compounds according to this invention at increasing doses to batches of ten female mice EOPS (CESAL breeding) according to the technique of D. E. J. Campbell and W. Richter (Acta Pharm and Toxicol. 25 (1967) 345). The animals are kept under survey for 5 days and the deaths if any, are numbered.

The obtained results show that the average lethal doses range from 360 mg/kg to 1200 mg/kg depending on the compounds.

(B) Determination of the Anti Hypertensive Action

This test is carried out in batches of awake male Rats rendered hypertensive by ligation of the abdominal aorta.

The compounds according to this invention are given by oral way at a dose of 1.2 and 5 mg/kg. They produce a clear and protracted decrease of the blood pressure.

Moreover these compounds when intravenously-given to normo-tensive rats or to normotensive dogs previously anesthetized at doses ranging from 2 to 10 μg/kg for the most active compounds and from 20 to 50 μg/kg for the other compounds, induce a very marked hypotension.

(C) Search of a Vasodilating Effect

The compounds according to this invention do not cause any pertipheral vasodilating effect.

At the tested doses not any vasodilation or any increase of the cutaneous temperature of the hind feet of the rat has been evidenced.

What we claim is:

1. A compound selected from the group consisting of a 2-amino 5-(aralkylpiperidino alkyl)amino 1,4-diazole of the formula I $$Ar-X-N\underset{\diagup}{\overset{\diagdown}{\bigcirc}}-(CH_2)_{n'}-NH-Het \quad (I)$$

wherein Ar is a cyclic radical selected from the group consisting of pyridine, oxazine, pyrazine and a phenyl radical of the formula $$(R)_p\text{—}\bigcirc$$

wherein R is hydrogen, a lower alkyl radical, a lower alkoxy radical, wherein lower alk is 1-6 carbons, a halogen, a trifluoromethyl, a sulphonamido radical, a trifluoromethoxy, a cyano radical, a carboxy radical, a carboxamido radical, a nitro group or an alkylene dioxy a group of 2-4 carbon atoms, and p is an integer of 1 to 3, tetrahydronaphthyl, naphthyl-1, -2, benzodioxanyl, benzodioxenyl, quinolinyl, thiachromanyl, indolyl-2 and indolyl-3 and a bicyclic hydroaryl radical of the formula $$(R_1)_n\text{—}\underset{Y}{\overset{Y'}{\bigcirc\bigcirc}}$$

wherein Y and Y' are the same or different and are a $CH_2$- radical, O, S or NH X is an alkylene chain selected from the group consisting of
a $(CH_2)_n$ radical
a $CHOH-(CH_2)_{n_1}$ radical
a $CO-(CH_2)_{n_1}$ radical and $$-\underset{K}{\overset{\|}{C}}-(CH_2)_{n_1}$$

radical
in which n is equal to 1, 2, 3 or 4
$n_1$ is equal to 1, 2 or 3
n' is equal to zero, 1 or 2
K is a group $$\underset{\diagdown OR_2}{\overset{\diagup OR_1}{}}$$

wherein $R_1$ and $R_2$ are each a lower alkyl radical which may be the same or different, a lower alkylene chain, two hydrogens, $$\overset{O}{\diagup\!\!\!\diagdown} \quad \text{or} \quad \overset{H}{\diagdown\!\!\!\diagup}_{OH},$$

wherein lower alk is 1 to 6 carbon atoms and Het is a heterocyclic radical selected from the group consisting of the amino triazoles of formula A $$\underset{N}{\overset{R_3-N\text{———}N}{\underset{\|}{\bigtriangleup}}}\underset{NH_2}{\overset{\|}{}}$$

wherein $R_3$ is hydrogen, a lower alkyl radical of 1 to 6 carbon atoms, and the 1,4- diazoles of the formula $$\underset{N}{\overset{N\text{———}Z}{\underset{\|}{\bigtriangleup}}}\underset{NH_2}{\overset{\|}{}}$$

wherein Z is a —NH—radical, $NR_3$— or an oxygen and $R_3$ being defined as above and a pharmaceutically acceptable addition salt thereof with a mineral or organic acid.

2. An optically active isomer of the compound according to claim 1.

3. A compound according to claim 1 having the formula IA

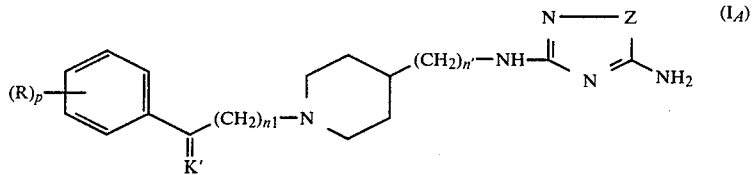

wherein K' is two hydrogens, the group

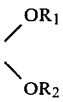

wherein $R_1$ and $R_2$ are defined as in claim 1 consisting of the group

or the oxygen of a Ketonic function $n_1$ and $n'$ are as defined in claim 1, and Z is a —NH or —$NR_3$ group or an oxygen wherein $R_3$ is as defined in claim 1.

4. A compound according to claim 1 having the formula IB

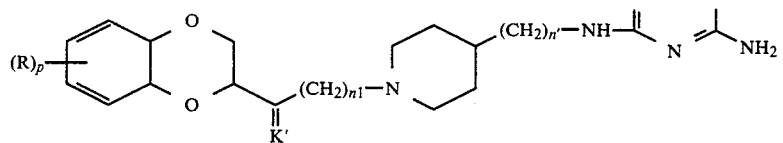

in which the substituents R, $R_3$, K', p, $n_1$ and $n'$ have the meanings of claim 1.

5. A compound according to claim 1 having the formula IC

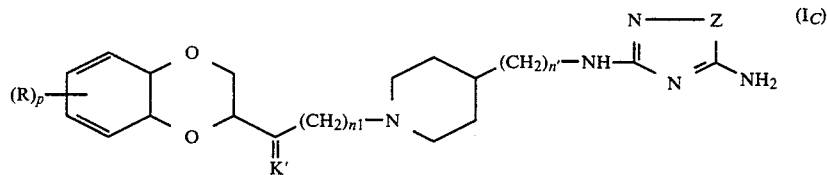

in which the substituents R, K, Z, p, $n_1$ and $n'$ have the meanings of claim 1.

6. A compound according to claim 1 having the formula ID

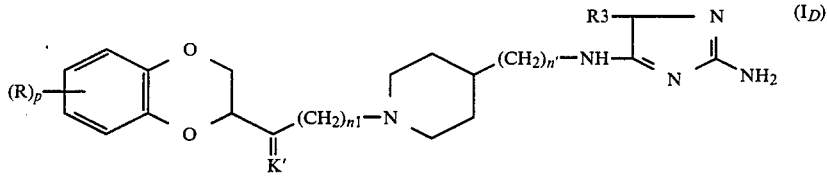

in which the substituents R, K, p, $n_1$, $n'$ and $R_3$ have the meanings of claim 1.

7. A compound according to claim 1 having the formula IE

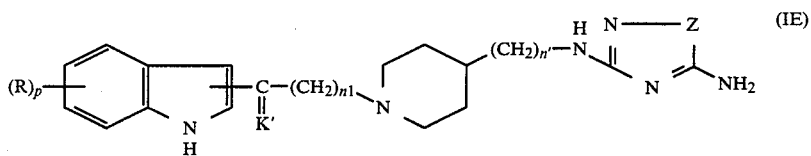

in which the substituents R, K', p, Z, $n_1$ and $n'$ are defined as in claim 1.

8. A compound according to claim 1 selected from the group consisting of 1-[(4-p-fluorophenyl-4-oxo)butyl-1)]-4-[(2-amino-4-methyl-1,3,4-triazolyl-5)aminomethyl]piperidine and hydrochloride salts thereof.

9. A pharmaceutical composition for treating hypertension containing as active ingredient an antihypertensively effective amount of at least one compound according to claim 1 in adjunction or in admixture with an inert non-toxic pharmaceutically acceptable carrier or vehicle.

10. A pharmaceutical composition according to claim 9 in one of the forms suitable for parenteral, oral, rectal or sublingual ways of administration.

* * * * *